United States Patent
Baecke et al.

(10) Patent No.: US 7,367,338 B2
(45) Date of Patent: May 6, 2008

(54) METHOD FOR COMPENSATING A PRESSURE DROP IN A VENTILATOR TUBE, VENTILATOR AND MEMORY MEDIUM

(76) Inventors: Martin Baecke, Lindenstr 7, Dessau (DE) 06847; Ewald Anger, Lindelbacher Strasse 10, Eibelstadt (DE) 97246; Jürgen Reinstädtler, Kapellenweg 2E, Wurzburg (DE) 97082

( * ) Notice: Subject to any disclaimer, the term of this patent is extended or adjusted under 35 U.S.C. 154(b) by 337 days.

(21) Appl. No.: 11/132,544

(22) Filed: May 19, 2005

(65) Prior Publication Data
US 2005/0241640 A1 Nov. 3, 2005

Related U.S. Application Data

(63) Continuation of application No. PCT/DE03/03592, filed on Oct. 29, 2003.

(51) Int. Cl.
*A61M 11/00* (2006.01)
(52) U.S. Cl. ............ 128/204.22; 128/203.14; 128/203.29; 128/204.21
(58) Field of Classification Search ........... 128/200.24, 128/203.14, 204.22, 203.29, 204.18, 204.21, 128/204.23, 204.26, 848
See application file for complete search history.

(56) References Cited

U.S. PATENT DOCUMENTS 7,077,131 B2 * 7/2006 Hansen ............... 128/204.18
7,168,429 B2 * 1/2007 Matthews et al. ..... 128/204.21

FOREIGN PATENT DOCUMENTS

DE 198 49 571 5/2000
WO WO 00/66207 11/2000

OTHER PUBLICATIONS

Avram R. Gold, MD; Alan R. Schwartz, MD, "The Pharyngeal Critical Pressure," Chest/110/4, Oct. 1996, pp. 1077-1088.
Alan R. Schwartz; James A. Rowley; David C. Thut; Solbert Permutt; Philip L. Smith, "Structural Basis for Alterations in Upper Airway Collapsibility," Sleep, 19(10), pp. S184-S188.

* cited by examiner

*Primary Examiner*—Steven O. Douglas
(74) *Attorney, Agent, or Firm*—King & Schickli, PLLC

(57) ABSTRACT

The present invention relates to a method of compensating the pressure drop in an ordinary ventilator tube. The method comprises the measurement of a first air flow at a first pressure on the apparatus' side of the ventilator tube and with the respiratory mask taken off. Moreover, a parameter is calculated in a function which provides the pressure drop in the ventilator tube in dependence on the air flow. The parameter for the air flow and pressure is calculated. Later, the air flow is calculated with the respiratory mask being put on. By means of the function a correction pressure is calculated from the air flow. Finally, a target pressure is set which results as a sum of the selected mask pressure and the correction pressure. The invention moreover relates to ventilator for performing the aforementioned method and to a memory medium for storing a corresponding program.

16 Claims, 3 Drawing Sheets

METHOD FOR COMPENSATING A PRESSURE DROP IN A VENTILATOR TUBE, VENTILATOR AND MEMORY MEDIUM

CROSS REFERENCE TO RELATED CO-PENDING APPLICATIONS

This application is a continuation of international application number PCT/DE03/003592 (publication number: WO 2004/045670 A2) filed on Oct. 29, 2003 and entitled METHOD FOR COMPENSATING A PRESSURE DROP IN A VENTILATOR TUBE, VENTILATOR AND MEMORY MEDIUM and claims the benefit of the above-mentioned international application and the corresponding German national patent application number 102 53 947.2-09 filed on Nov. 19, 2002 and entitled VERFAHREN ZUR KOMPENSATION DES DRUCKABFALLS AN EINEM BEATMUNGSSCHLAUCH, BEATMUNGSGERÄT SOWIE SPEICHERMEDIUM the contents of which are expressly incorporated herein by reference.

FIELD OF THE INVENTION

According to a first aspect the invention relates to a method for ventilator for the compensation of a pressure drop in a ventilator tube. The invention moreover relates to a ventilator performing such a method, and to a memory medium for storing a corresponding program.

BACKGROUND OF THE INVENTION

Known are ventilators or respirators for the mechanical, artificial respiration for all forms of an oxygen deficiency state. They are, inter alia, applied for the long-time respiration. (Roche Medical Dictionary, 4$^{th}$ Edition, edited by Hoffmann-La Roche AG and Urban & Fischer, Urban & Fischer, Munich, Stuttgart, Jena, Lübeck, Ulm).

A particular form of ventilator, so-called CPAP apparatus, are used to avoid obstructive respiratory disturbances during sleep.

Obstructive respiratory disturbances result in apneas which make the sleeping person wake up. Frequent apneas prevent the sleeping person from falling into the relaxing deep sleep. People suffering from apneas during sleep therefore are tired during the day, which may result in social problems at work and, in the worst case, in deadly accidents, for example with professional motorcar drivers.

The CPAP (continuous positive airway pressure) therapy was developed for the treatment of apneas and is described in Chest. Volume No. 110, pages 1077-1088, October 1996 and in Sleep, Volume No. 19, pages 184-188. A CPAP-apparatus generates a positive overpressure up to approximately 30 mbar by means of a fan and administers said positive pressure, preferably via a humidifier, via a ventilator tube and a nose or face mask to the respiratory tract of the patient.

This positive pressure is to ensure that the upper respiratory tract remains fully opened during the whole night, so that no apneas will occur (DE 198 49 571 A1). The required positive pressure is also called therapeutic pressure $p_t$ and depends, inter alia, on the sleeping stage and the position of the body of the sleeping person.

FIG. 1 shows a CPAP-apparatus 1 during therapeutic use. The CPAP-apparatus 1 comprises a housing 4, a ventilator tube 9, and a nose or face mask 18. The housing 4 includes a fan 8 also being called a compressor, blower, ventilator or turbine. A pressure sensor 11 for measuring the positive pressure, generated by the fan, with respect to the ambient pressure is provided in the proximity of the ventilator tube connection inside the housing. The measured positive pressure will hereinafter be called actual pressure. The air conveyed by the fan 8 is supplied via a ventilator tube 9 to the face mask 18 worn by the patient 19 himself. In the face mask 18, or in the proximity thereof, an expiration opening 2 is provided, through which a permanent air flow occurs from the ventilator tube into the ambiance. This air flow ensures that the air expired by the patient is carried off into the ambiance and prevents the accumulation of $CO_2$ in the ventilator tube 9. A microcontroller 5 controls the number of revolutions of the fan such that the actual pressure measured by the pressure sensor 11 corresponds to a target pressure.

With all known CPAP-apparatus, and according to the patent literature, so far two methods are used so as to determine the pressure in the face mask of CPAP-apparatus.

According to one thereof a pressure sensor detects the pressure of the air conveyed to the patient directly in the apparatus. In the factory, for a frequently used combination of ventilator tube and mask the pressure difference is measured at a medium volume flow. This differential value is deducted from the pressure measured in the apparatus, and the result is interpreted as mask pressure. Errors in the pressure adjustment are inevitable because the air flow permanently fluctuates due to the respiration so that the pressure loss in the ventilator tube varies. It is thereby particularly annoying for the patient that the pressure in the face or nose mask is lower during inspiration as compared to expiration. Particularly with this form of pressure control the patient therefore has the feeling that he has to respire against a resistance.

According to other methods, one of which is described in WO 00/66207, the detection of the pressure is effected in the proximity of the end of the ventilator tube in front of the mask or in the mask. The pressure detection is thereby very exact. The pressure control also compensates leakages etc. The pressure measurement itself may be accomplished with a pressure sensor the electrical connecting leads of which have to be guided with the ventilator tube to the ventilator. In particular with apparatus from MAP is a separate thin tube guided from the measuring point to a pressure sensor disposed in a CPAP-apparatus. A drawback of these variants resides in that special tubes are necessary so as to bring the connecting leads or the tube, respectively, back into the CPAP-apparatus. These custom-made products are more expensive than ordinary ventilator tubes. Moreover, their use with other CPAP-apparatus is possible only to a limited extent. Finally, the cleaning is more complicated.

SUMMARY OF THE INVENTION

According to an embodiment of the invention a method of compensating the pressure drop in a ventilator tube is provided. A first air flow at a first pressure on the apparatus' side of a ventilator tube is measured with the respiratory mask taken off. A parameter in a function providing the pressure drop in said ventilator tube in dependence on the air flow is calculated. The parameter for the first air flow and the first pressure is calculated. Then the air flow with the respiratory mask being put on is measured. A correction pressure by means of the function for the measured air flow is calculated. A target pressure is determined as sum of the selected mask pressure and the correction pressure. This target pressure is set.

According to another embodiment of the invention a ventilator is provided. The ventilator comprises a housing, a fan within said housing, a mask, a ventilator tube, a flow sensor and a controller. The ventilator tube connects said fan and said mask. The flow sensor measures an air flow in said ventilator tube; said flow sensor measuring a first air flow at a first pressure while the respiratory mask is being taken off. The controller calculates a parameter in a function which provides the pressure drop in said ventilator tube in dependence on the air flow. The parameter for the first air flow and the first pressure is calculated. The flow sensor measures the air flow with the respiratory mask being put on. The controller calculates a correction pressure by means of the function for the measured air flow. The controller sets a target pressure determined as sum of the selected mask pressure and the correction pressure.

According to a further embodiment of the invention a memory medium for use with a CPAP-apparatus. The memory medium stores commands. The CPAP-apparatus, comprises a central processing unit for processing the commands stored in the memory medium. During the processing of the commands stored in the memory medium the CPAP-apparatus measures a first air flow at a first pressure on the apparatus' side of a ventilator tube with the respiratory mask taken off. The CPAP-apparatus calculates a parameter in a function providing the pressure drop in said ventilator tube in dependence on the air flow, wherein the parameter for the first air flow and the first pressure is calculated. The CPAP-apparatus measures the air flow while the respiratory mask is being put on and calculates a correction pressure by means of the function for the measured air flow. The CPAP-apparatus sets a target pressure determined as sum of the selected mask pressure and the correction pressure.

An advantage of the invention resides in that the costs of production of the CPAP-apparatus are reduced because no special ventilator tubes have to be used.

An advantage in the measurement of the air flow at two different pressures resides in that the two parameters C and a in equation 6 are determined on the basis of measured values, so that the pressure drop determined for a measured flow during the therapy corresponds to the actual pressure drop in the ventilator tube more exactly.

The higher the number of pressures is, at which the flow is measured during the initializing phase when the respiratory mask is taken off, the more exact is the pressure compensation during the therapy.

The fitting of the parameter C or the parameters C and a to a plurality of pressure and flow values reduces the influence of possible outliers on the measured values and avoids the searching expenditure for the correct interval for a function defined section-wise.

The rejection of pressures measured during the initialization reduces the memory expenditure in an advantageous manner. By the section-wise fitting of the parameter C or the parameters C and a in equation 6 to intervals, at the lower and upper end of which both the pressure and the flow were measured, results in a very exact correspondence between the calculated and the actual pressure drop in the ventilator tube. Outliers in the pressure or flow measurement only influence the adjacent intervals.

The criterion to discontinue the initializing phase given a significant difference between the target pressure and the actual pressure is advantageous, because by this the entire available flow range is covered by measuring points, and it is avoided that several measuring points are recorded with a maximum flow. The latter entails an unnecessarily long initialization.

The control, whether the parameter C is in a reasonable range, already during the measurement of the pressure and flow values during the initializing phase and the discontinuance of the initializing phase, if the parameter C is not in a reasonable range, ensures, for example, that the patient has not put on the mask during the initialization already.

The use of a stored parameter value is a sensible fallback position if the initialization cannot be performed. This is the case, for example, when the patient has put on the mask already while the apparatus is turned off.

The use of actual pressure values instead of target pressure values according to the inventive method avoids errors with deviations between the actual pressure and the target pressure.

BRIEF DESCRIPTION OF THE DRAWINGS

Preferred embodiments of the invention will hereinafter be explained in more detail with reference to the enclosed drawings, wherein like numerals represent like parts.

DETAILED DESCRIPTION OF THE INVENTION

As was mentioned above, the pressure drop in the ventilator tube fluctuates with the air flow through the ventilator tube. The air flow, again, changes during a respiratory cycle. It is high in particular during inspiration and low during expiration, and may even change its sign during expiration. If only the pressure supplied by the ventilator is kept constant, the pressure in the respiratory mask is higher during expiration as compared to inspiration, which is unpleasant for the patient. In this respect the invention takes corrective measures in that the desired therapeutic pressure $p_t$, which is to be equal to the mask pressure $p_m$, if possible, is corrected by the pressure drop in the tube. The sum of the therapeutic pressure $p_t$ and the pressure drop $\Delta p$ is set as target pressure p:

$$p = p_s + \Delta p \quad (1)$$

The pressure drop $\Delta p$ is a function of the air flow:

$$\Delta p = f(\dot{V}) \quad (2)$$

For measuring the air flow the CPAP-apparatus according to the invention is equipped with an air flow sensor 16. The air flow sensor 16 can determine the air flow on the basis of the thermal loss of a heating filament 17. As was mentioned above, the air flow fluctuates with the respiration of the patient. The pressure drop $\Delta p$ therefore is to be calculated more often during a respiratory cycle. A respiratory cycle typically lasts between 3 and 5 seconds so that the pressure drop and the target drop are to be calculated at least twice per second.

Figure 1:
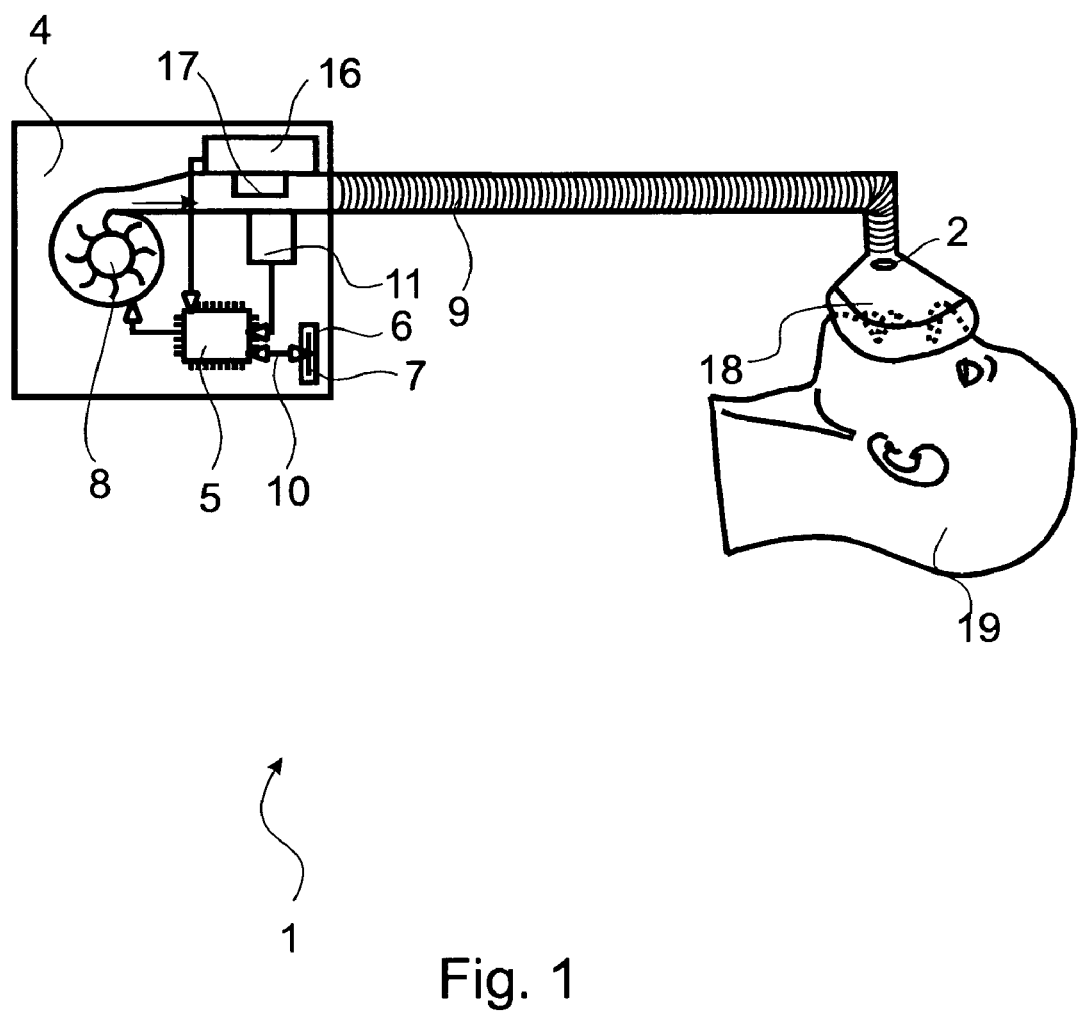
FIG. 1 shows a CPAP-apparatus.
Figure 2:
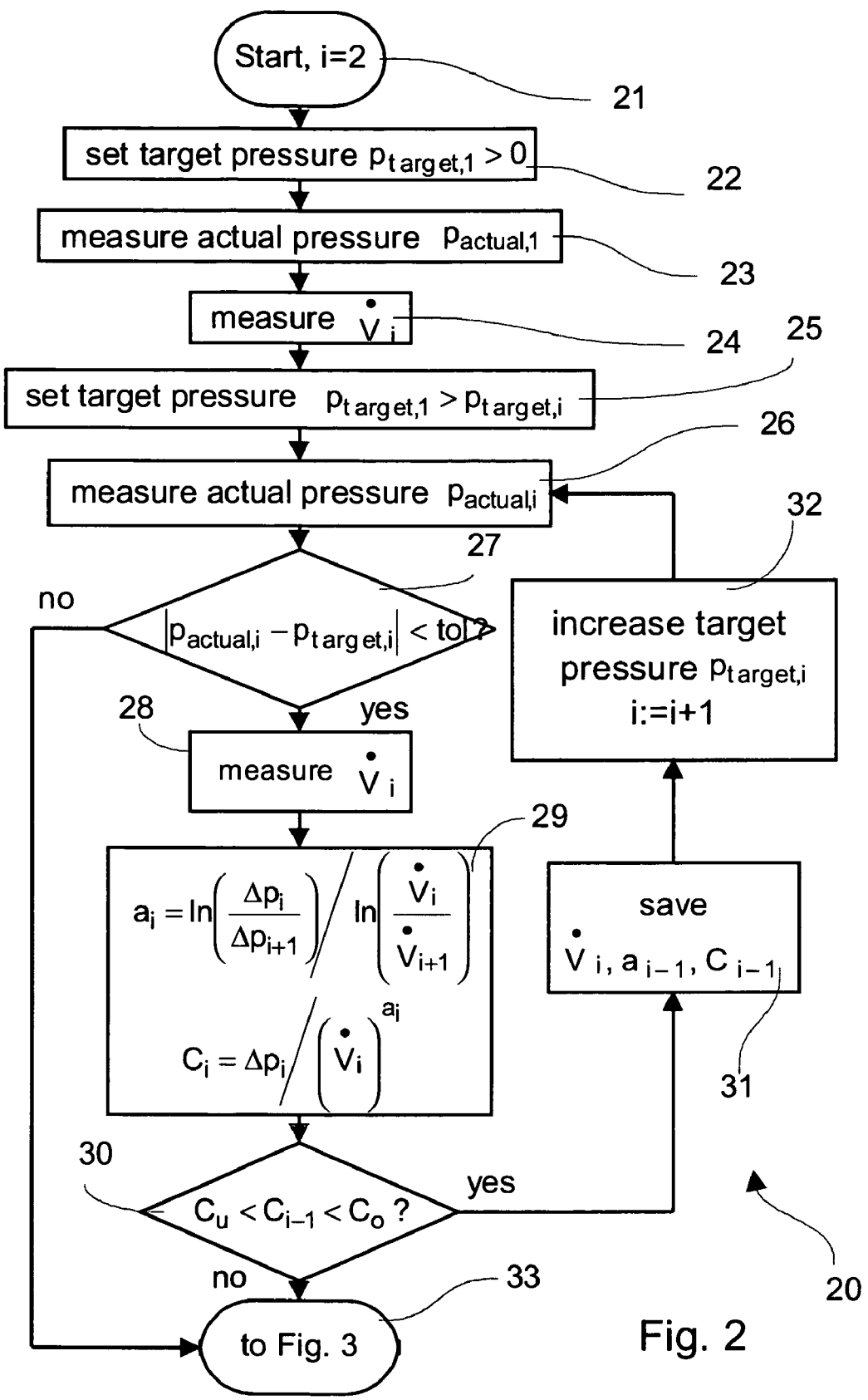
FIG. 2 shows a flow diagram of an initialization method according to the invention.

According to the invention an initialization is performed after the apparatus is switched on and before the patient 19 puts on the respiratory mask 18. The flow diagram of the initialization is illustrated in FIG. 2. If the mask is taken off, the mask pressure $p_m$ is equal to the ambient pressure. From this results that the pressure measured on the pressure sensor 11 is equal to the pressure drop $\Delta p$ in the ventilator tube. According to an embodiment the target pressure is increased in several steps (step 32) up to a maximum value during the initialization, and the actual pressure $\Delta p_i$ and the air flow $\dot{V}_i$ (steps 26, 28, 28) are measured in each step. After the initialization the measured pressure and flow values $\Delta p_i$ and $\dot{V}_i$, respectively, can be stored for further use.

During the therapy, i.e. when the patient has put on the respiratory mask 18, the nearest air flow $\dot{V}_i$ measured during the initialization can be searched for with respect to a measured air flow $\dot{V}$ so that the pressure drop results as $\Delta p_i$. It may also occur that negative flows are measured during the expiration phase. In this case $\dot{V}_i$ nearest to the absolute value of $\dot{V}$ is searched for and $\Delta p_i$ receives the sign of the measured flow. A drawback of this method resides in that plenty of pressure and flow values have to be measured during the initialization so as to allow a sufficiently exact determination of the pressure drop.

In order to be able to do with fewer pressure and flow values the pressure drop $\Delta p$ between the measured flow values can be calculated, for example, by linear interpolation according to equation (3). However, before applying equation (3), the index i still has to be determined, i.e. the correct interval for the measured flow $\dot{V}$ must be found.

$$\Delta p(\dot{V}) = \Delta p_i + \frac{\Delta p_{i+1} - \Delta p_i}{\dot{V}_{i+1} - \dot{V}_i}(\dot{V} - \dot{V}_i) \text{ wherein } \dot{V}_i \leq \dot{V} < \dot{V}_{i+1} \quad (3)$$

The factor sign $(\dot{V})$ thereby either adopts value 1 for an air flow to the patient or −1 for an air flow from the patient so as to take into account the direction of the flow.

The linear interpolation merely is a mathematical method which can be applied in general, however, which ignores the physical backgrounds of the air flow through a tube.

For further reducing the number of required measured values $\Delta p_i$ and $\dot{V}_i$ the pressure drop in a tube such as the ventilator tube 9 can be calculated from the following formula (Technische Strömungsmechanik 1, VEB Deutscher Verlag für Grundstoffindustrie, Leipzig):

$$\Delta p = \xi \frac{\rho}{2} v^a = \frac{\lambda l}{d} \cdot \frac{\rho}{2} v^a \cdot \text{sign}(v) \quad (4)$$

$\Delta p$ thereby is the pressure dropping in the tube, $\xi$ is a pressure loss correction value of the tube, $\lambda$ is a pipe friction value of the tube, l is the length of the tube, d is the diameter of the tube, $\rho$ is the density of the flowing medium, i.e. in CPAP-apparatus approximately 1.2 kg/m³ for air, and v is the flow velocity from the CPAP-apparatus in the direction of the mask averaged over the cross-section. a has the value 2 for turbulent flows and 1 for laminar flows. In practice a may also adopt intermediate values, as an ideal-typical form of flow is rare. Under the typical conditions of CPAP-apparatus turbulent flows are prevailing, so that a≈2. Equation (4) is also known from Strömungslehre, J. H. Spurk, 4$^{th}$ Edition, Springerverlag, Berlin 1996, wherein $\lambda$ here is called the flow resistance coefficient. The averaged flow velocity is connected with the air flow $\dot{V}$ as follows:

$$\dot{V} = v \cdot \pi \cdot (d/2)^2 \quad (5)$$

V itself stands for an air volume. The point designates the derivative with respect to time d/dt. $\dot{V}$ is detected by the flow sensor 16.

If one inserts (2) in (1), one obtains the following quadratic dependence of the pressure drop $\Delta p$ on $\dot{V}$. The dependencies of $\lambda$, l, d and $\rho$ were combined to the constant C, with C being a parameter for the used tube:

$$\Delta p = C \cdot |\dot{V}|^a \cdot \text{sign}(\dot{V}) \quad (6)$$

Equation (6) contains the two parameters C and a. Therefore, at least two measuring points at different pressures $\Delta p_i$ and $\Delta p_{i+1}$ as well as the corresponding flow values $\dot{V}_i$ and $\dot{V}_{i+1}$ are required to determine both parameters. According to an embodiment the parameters $a_i$ and $C_i$ for the interval i can thus be determined for a flow $\dot{V}$ between $\dot{V}_i$ and $\dot{V}_{i+1}$ according to equations (7) and (8). The pressure drop $\Delta p$ then results from equation (9).

$$a_i = \frac{\ln\left(\frac{\Delta p_i}{\Delta p_{i+1}}\right)}{\ln\left(\frac{\dot{V}_i}{\dot{V}_{i+1}}\right)} \quad (7)$$

$$C_i = \frac{\Delta p_i}{(\dot{V}_i)^{a_i}} \quad (8)$$

$$\Delta p = C_i \cdot |\dot{V}|^{a_i} \cdot \text{sign}(\dot{V}) \text{ wherein } \dot{V}_i \leq \dot{V} < \dot{V}_{i+1} \quad (9)$$

As can be seen from equation (9) the measured pressure values of the $\Delta p_i$ here no longer occur. After the initialization, therefore, merely the flow values $\dot{V}_i$ and the parameter values $C_i$ and $a_i$ have to stored for further use (step 31).

According to another embodiment the parameter a may be set at a value between 1 and 2. Only parameter $C_i$ is separately calculated from equation (8) for each interval. In this embodiment only the one value a for all $a_i$ and the values $C_i$ and $\dot{V}_i$ are stored for the subsequent therapeutic phase.

The pressure and flow values $\Delta p_i$ and $\dot{V}_i$, respectively, measured during the initialization are to cover preferably the entire flow range without, however, measuring the same actual pressure and flow several times at the upper end because the ventilator cannot supply enough air so that the actual pressure cannot continue to follow the target pressure. For this reason it is checked in step 27 whether a target pressure set by the microcontroller 5 and an actual pressure measured by the pressure sensor 11 differ from one another by less than the tolerance tol. If this is the case, additional pressure and flow pairs may be measured in steps 28 and 26. If this is not the case, the initialization is stopped in step 33.

Preferably the parameters $a_i$ and $C_i$, or only $C_i$, are calculated for each measurement interval in step 29 according to equations (7) and (8) already during the initialization. Thus, it can be checked in step 30, whether the parameter $C_i$ for an interval i+1 is within an allowed range between a lower value $C_u$ and an upper value $C_o$. As was mentioned above, the parameter C combines the flow resistance coefficient $\eta$, the length of the tube l as well as the diameter of the tube d. C thus constitutes sort of a resistance of the tube. If, for example, the patient puts on the mask during the initialization, the calculated resistance value increases because it now forms a series connection of the tube 9 and the expiration opening 2. Thus, step 30 constitutes a plausibility control as to whether correct values are still being measured. If the initialization is stopped in step 30, the values $\dot{V}_i$, $C_{i-1}$ and possibly $a_{i-1}$ measured until then are stored, and the values of a preceding initialization or preprogrammed standard values are used for higher flows.

As equation (6) describes a pressure drop in a tube in a broad flow range in good approximation it may sufficient that a measurement of the flow $\dot{V}_i$ be effected at merely two different pressure values $\Delta p_i$ so as to determine the parameters a and C for the complete flow range. None of the pressures or flows must be zero since it must not be divided by zero in equation (7) and the logarithm of zero is not defined. Also, the flows must be different. Otherwise, their proportion is 1, the logarithm of 1 is zero and a division by zero must not be made. This is the reason for steps 22 to 24 preceding the loop, in which a pair of pressure/flow variates is measured before the calculation of $C_1$.

According to another embodiment the parameter a may be predefined by the factory, and merely the flow with respect to a single actual pressure Δp may be determined. From this, merely a parameter C is calculated according to equation (8).

According to another embodiment n pairs of pressure/flow variates $\Delta p_i$ and $\dot{V}_i$ can be measured, wherein $n \geq 3$. To these pairs of variates the parameters C and a, or only C, can be fitted in equation (6). In this embodiment fluctuations in the measured values, which may be due to noise, are compensated. Also, the measuring points may be divided into several intervals, with each interval containing at least three measuring points. For each interval i either one parameter $C_i$ only, or a parameter $C_i$ and a parameter $a_i$ may be fitted.

Figure 3:
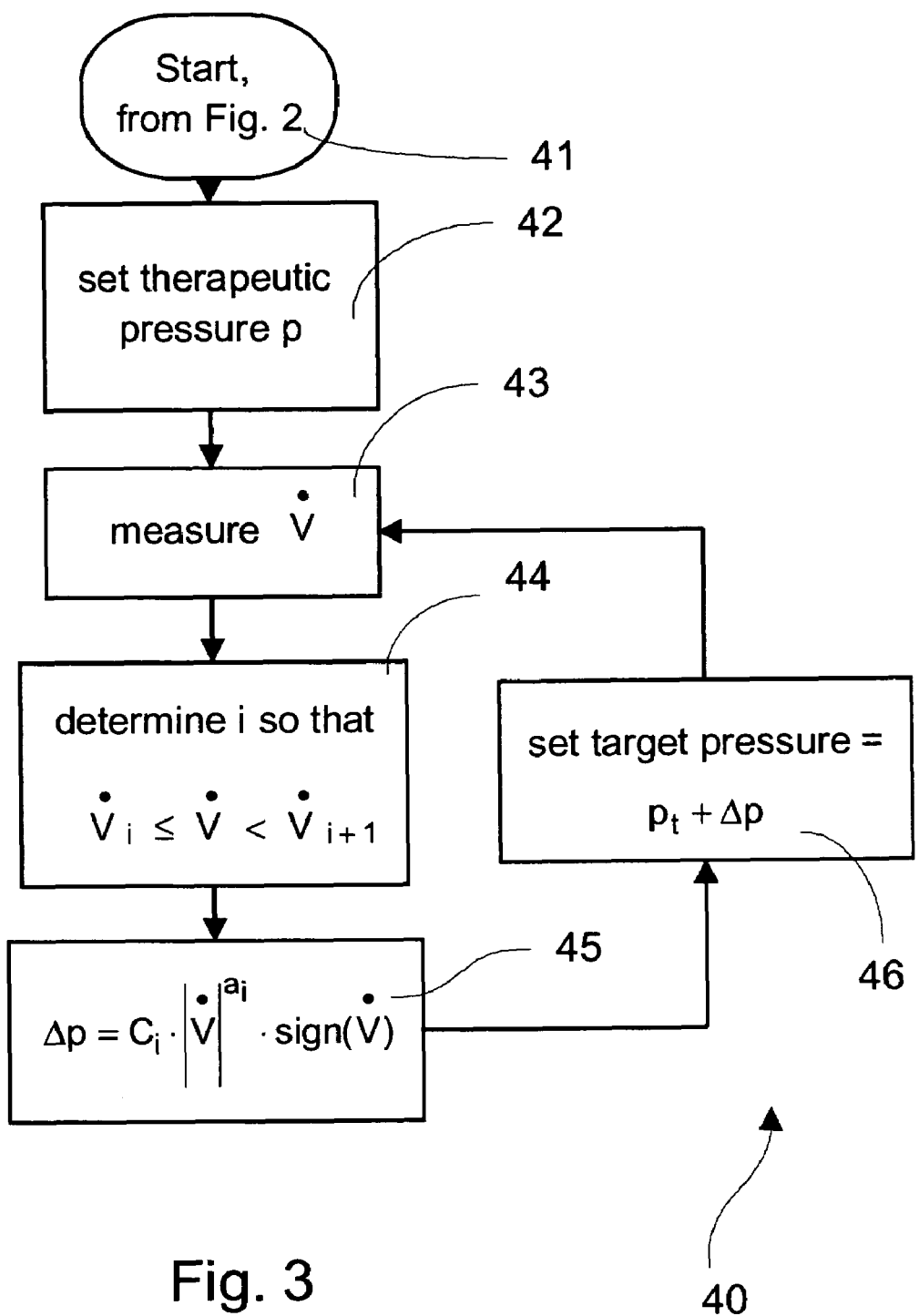
FIG. 3 shows a flow diagram of a method according to the invention for compensating the pressure drop in a ventilator tube.

FIG. 3 shows the behavior of a ventilator, in particular of a CPAP-apparatus, during therapy. After the start in step 41 a therapeutic pressure $p_t$ is set in step 42 which may, as was mentioned above, be predefined by a medical practitioner, for example. At this therapeutic pressure the air flow is measured by a flow sensor 16 in step 43. If the function for the calculation of the pressure drop Δp from the flow $\dot{V}$ is defined section-wise as in equation (9), the correct interval i is determined for the measured air flow $\dot{V}$ in step 44. If, for example during inspiration, the flow $\dot{V}$ exceeds the highest flow value $V_n$ measured during the initialization the parameters for the highest interval n−1 are used. Subsequently, the pressure drop is determined in step 45 by means of equation (9), whereupon, in step 46, a new target pressure is calculated from equation (1).

Subsequently, the flow measurement is repeated in step 43. The endless loop formed of steps 43, 44, 45 and 46 is, as was mentioned above, looped at least twice per second so that the target pressure fluctuates in correspondence with the respiratory cycle of the patient allowing to compensate the pressure drop in the ventilator tube in real-time. Apart from the loop illustrated in FIG. 3 another pressure control loop is provided, as was mentioned above, which controls the speed of the turbine such that the pressure measured by the pressure sensor 11 corresponds to the set target pressure p as exactly as possible.

In the CPAP-apparatus according to the invention the steps shown in FIGS. 2 and 3 are executed by the microcontroller 5. For changing the programming thereof, the microcontroller may be connected to a plug-in slot 7 via a data line 10 into which a memory medium 6 is plugged. This may be a memory stick or a PCMCIA card. The plug-in slot 7 may, however, be an IC socket for a PROM component (PROM: programmable read only memory). According to another embodiment the microcontroller 5 may include an EPROM (electrical PROM). In this case, the microcontroller itself is the memory medium which may be exchanged.

In the foregoing, the invention was explained in more detail by means of preferred embodiments. It is, however, obvious for the person skilled in the art that various alterations and modifications may be made without departing from the spirit of the invention. Therefore, the scope of protection is defined by the following claims and their equivalents.

LIST OF REFERENCE NUMERALS

1 CPAP-apparatus
2 expiration opening
4 housing
5 microcontroller
6 memory medium
7 plug-in slot
8 fan
9 ventilator tube
10 data line
11 pressure sensor
16 flow sensor
17 heating filament
18 face mask
19 patient
20 initialization
21-33 steps
40 therapy
41-46 steps

What is claimed is:

1. A method of compensating for a pressure drop in a ventilator tube associated with a respiratory mask having a selected mask pressure, comprising:
   measuring a first air flow at a first pressure on a ventilator side of a ventilator tube and with the respiratory mask taken off;
   calculating a first parameter in a function providing the pressure drop in said ventilator tube in dependence on air flow;
   measuring a second air flow with the respiratory mask being put on;
   calculating a correction pressure by means of the function for the measured first and second air flows; and
   setting a target pressure determined as sum of the selected mask pressure and the correction pressure.

2. The method according to claim 1, further comprising:
   measuring a third air flow at a third pressure on the ventilator side unequal to the first pressure and with the respiratory mask taken off;
   calculating the first parameter and a second parameter of the function, wherein both the first and second parameters are calculated from the first and third air flows and the first and third pressures.

3. The method according to claim 1, further comprising:
   setting a plurality of pressures on the ventilator side of a ventilator tube with the respiratory mask taken off;
   measuring the first air flow at each of the plurality of pressures; and
   calculating correction pressures by means of the function for the measured first air flows at each of the plurality of pressures.

4. The method according to claim 3, further comprising:
   calculating the first parameter of the function such that the correction pressures calculated from said measured air flows by said function correspond to the set pressures.

5. The method according to claim 1, further including the step of storing the first parameter, but not the first pressure measured with the respiratory mask taken off.

6. The method according to claim 3, wherein for each interval between two first air flows measured with the respiratory mask taken off, the first parameter for the function is calculated from the first air flows limiting the interval and the corresponding pressures and, when calculating the correction pressures, at first the interval between two pressures measured with the respiratory mask taken off is searched and used in the function for the interval.

7. The method according to claim 3, wherein during the setting of the plurality of pressures, the pressures increase monotonously and no further pressures are set, if the difference between a predefined target pressure and a measured actual pressure exceeds a predetermined value.

8. The method according to claim 6, wherein the first parameter for a flow interval is calculated after both first air flows were measured at the interval boundaries and the corresponding pressures were set and before another pressure is set, wherein another pressure is set only if said first parameter is within a predefined interval.

9. The method according to claim 1, further including the step of checking whether the calculated parameter is within a predefined range and, if this is not the case, using a stored parameter value as the first parameter in the function.

10. The method according to claim 1, wherein actual pressure values measured by a pressure sensor are used for calculating the parameter(s).

11. A ventilator, comprising:
a housing;
a fan within said housing;
a respiratory mask having a selected mask pressure;
a ventilator tube having a ventilator side, said ventilator tube connecting said fan and said respiratory mask;
a flow sensor for measuring a first air flow at a first pressure on the ventilator side of said ventilator tube while the respiratory mask being taken off;
a controller for calculating a first parameter in a function providing a pressure drop in said ventilator tube in dependence on air flow;
said flow sensor also for measuring a second air flow while the respiratory mask being put on;
said controller calculating a correction pressure by means of the function for the measured first and second air flows; and
said controller setting a target pressure determined as sum of the selected mask pressure and the correction pressure.

12. The ventilator according to claim 11, said flow sensor measuring a third air flow at a third pressure unequal to the first pressure and with the respiratory mask taken off; said controller calculating the first parameter and a second parameter of the function, both parameters being calculated from the first and third air flows and the first and third pressures.

13. The ventilator according to claim 11, wherein the controller determines whether the target pressure and an actual pressure measured by a pressure sensor differ from one another by less than a predetermined tolerance value.

14. The ventilator according to claim 11, wherein the controller calculates the first parameter for a flow interval and sets the corresponding pressures before another pressure is set, wherein another pressure is set only if said first parameter is within a predefined interval.

15. The ventilator according to claim 11, wherein the controller checks whether the calculated first parameter is within a predefined range and, if this is not the case, a stored parameter value is used as the first parameter in the function.

16. A memory medium for use with a CPAP-apparatus associated with a respiratory mask having a selected mask pressure and comprising a central processing unit for processing the commands stored in the memory medium, the CPAP-apparatus performing the following steps during the processing of the commands stored in the memory medium:
measuring a first air flow at a first pressure on a ventilator side of a ventilator tube and with the respiratory mask taken off;
calculating a parameter in a function providing the pressure drop in said ventilator tube in dependence on the air flow;
measuring the air flow with the respiratory mask being put on;
calculating a correction pressure by means of the function for the measured air flow; and
setting a target pressure determined as sum of the selected mask pressure and the correction pressure.

* * * * *

UNITED STATES PATENT AND TRADEMARK OFFICE
CERTIFICATE OF CORRECTION

| | |
|---|---|
| PATENT NO. | : 7,367,338 B2 |
| APPLICATION NO. | : 11/132544 |
| DATED | : May 6, 2008 |
| INVENTOR(S) | : Baecke et al. |

Page 1 of 1

It is certified that error appears in the above-identified patent and that said Letters Patent is hereby corrected as shown below:

On the title page insert the following:

(30) Foreign Application Priority Data

Nov. 19, 2002    [DE] ------------------------- 102 53 947

Signed and Sealed this

Fifteenth Day of July, 2008

JON W. DUDAS
*Director of the United States Patent and Trademark Office*